United States Patent [19]
Vachet

[11] Patent Number: 5,089,021
[45] Date of Patent: Feb. 18, 1992

[54] INTRA-ORBITAL IMPLANT MANUFACTURING METHOD AND INTRA-ORBITAL IMPLANT

[76] Inventor: Jean-Marc Vachet, 15 rue de Buci, 75006 Paris, France

[21] Appl. No.: 459,877

[22] Filed: Jan. 2, 1990

Related U.S. Application Data

[63] Continuation of Ser. No. 96,863, Sep. 15, 1987, abandoned.

[30] Foreign Application Priority Data

Sep. 15, 1986 [FR] France ............................... 86 12880

[51] Int. Cl.$^5$ ............................................. A61F 2/14
[52] U.S. Cl. ............................................. 623/4; 427/2
[58] Field of Search ........................ 623/4, 11; 427/2

[56] References Cited

U.S. PATENT DOCUMENTS

| | | | |
|---|---|---|---|
| 4,208,745 | 6/1980 | Okita | 623/1 |
| 4,647,282 | 3/1987 | Fedorov et al. | 623/4 |
| 4,731,077 | 3/1988 | Allen | 623/4 |
| 4,759,759 | 7/1988 | Walker et al. | 623/900 X |
| 4,955,907 | 9/1990 | Ledergerber | 623/11 X |

FOREIGN PATENT DOCUMENTS

| | | | |
|---|---|---|---|
| 1068052 | 12/1979 | Canada | 623/11 |
| 0176042 | 10/1965 | U.S.S.R. | 623/4 |
| 2178963 | 2/1987 | United Kingdom | 623/11 |

OTHER PUBLICATIONS

Neuhaus et al., "Enculeation with Implantation of a Proplast Sphere", *Ophthalmology*, May 1984, vol. A1, No. 5, pp. 494–496.

Primary Examiner—Randall L. Green
Assistant Examiner—David H. Willse
Attorney, Agent, or Firm—Pollock, Vande Sande & Priddy

[57] ABSTRACT

An intra-orbital implant (1) is made by integrally coating a spherical core (36) with a preferably flexible, biocompatible synthetic material by means of a uniform layer (3) of a microporous, bio-compatible synthetic material intimately mated to the spherical core (36). The layer (3) is formed, for example, by two identical strips (6, 7) of the material, disposed according to mutually perpendicular median planes (18, 19) each containing the spherical center of the core, the strips being joined to each other edge-to-edge. Used after enucleation or evisceration, such implants permit colonization by the natural tissue, thereby avoiding the risk of rejection.

15 Claims, 3 Drawing Sheets

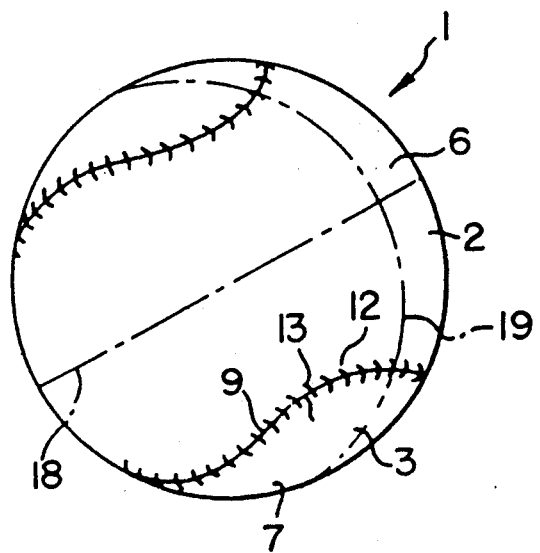
FIG_1
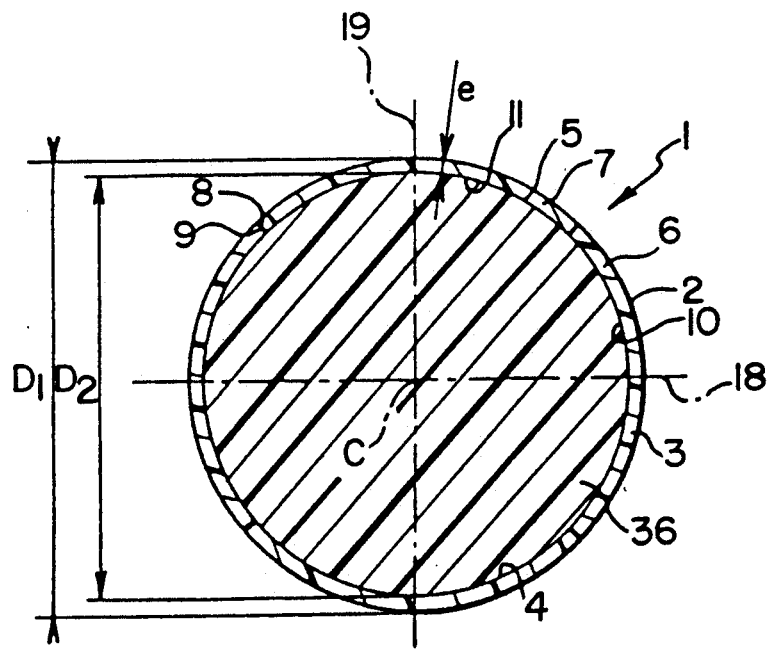
FIG_2

1

INTRA-ORBITAL IMPLANT MANUFACTURING METHOD AND INTRA-ORBITAL IMPLANT

CROSS-REFERENCE TO RELATED APPLICATION

This is a continuation of U.S. Pat. Application No. 07/096,863, filed Sept. 15, 1987, now abandoned.

FIELD OF THE INVENTION

The present invention concerns the manufacture of an intraorbital implant designed to be accommodated in an orbital cavity after enucleation or evisceration and to be connected to oculomotor muscles.

BACKGROUND OF THE INVENTION

Various types of implant of this kind have already been proposed, with the intention of obtaining not only anatomical but also, to some degree, functional reinstatement after enucleation or evisceration, in order to obtain the most satisfactory aestheric result possible after a prosthesis reproducing the appearance of the anterior segment of the enucleated eye has been fitted onto the implant.

Thus, U.S. Pat. No. 2,667,645 describes the manufacture of an implant from a bio-compatible, synthetic material spherical core over part of which is fixed a metal mesh corset enabling clips for attaching some of the motor muscles of the enucleated eye to be anchored to it. This implant has the disadvantage of lacking uniformity and sphericity, which limits its mobility in the orbital cavity and even creates the risk of trauma to and infection of the orbital cavity. Also, the oculomotor muscles are anchored to an implant of this kind in a purely mechanical way, so that there is a significant risk of the implant being rejected.

These disadvantages are found in most intra-orbital implants designed to be connected to oculo-motor muscles known at this time.

SUMMARY OF THE INVENTION

The object of the present invention is to propose the manufacture of an intra-orbital implant overcoming these disadvantages, using a bio-compatible synthetic material spherical core.

To this end, the present invention proposes a manufacturing method according to which all of the spherical core is coated with a substantially uniform layer of a micro-porous, bio-compatible synthetic material intimately mated to the spherical core.

The substantially uniform layer, by which is meant a layer cf substantially constant thickness and uniform appearance, with which all of the spherical core is coated, makes it possible to retain the spherical shape of the latter. Manufacture of this substantially uniform layer from a micro-porous, bio-compatible synthetic material, which advantageously consists of micro-porous polytetrafluorethylene of the type described in U.S. Pat. No. 3,953,566 and distributed under the trademark "GORE-TEX" or under the trademark "IMPRA", facilitates anchoring the muscles in an application to enucleation or the sclera in an application to evisceration, by enabling colonization of all of the thickness of the coating layer on the spherical core by fibroblasts and blood vessels, gradually transforming this layer into a tissue and vascular shell minimizing the risk of extrusion of the implant.

This layer is preferably fastened to the spherical core, by adhesive bonding, for example, or by suturing, i.e., by drawing together, by means of a single threaded needle, the two elements to be joined, the thread then pulling together the respective edges to form a suture edge. "Suturing," as used herein and as used as a term of art in surgery, is to be distinguished from other attachment techniques such as the drilling of holes into bone tissue or solid, inflexible material such as methacrylate, for the passage of wires or screws retaining a plate. Such tissues or materials are not "suturable." For example, it would be impossible to "suture" four muscles directly to a solid sphere; rather these would have to be sutured to each other in crossed pairs in front of the sphere.

The bio-compatible synthetic material of the spherical core is preferably flexible and consists, for example, of an elastomer chosen from the group comprising the silicone elastomers.

The micro-porous, bio-compatible synthetic material is also preferably flexible, which is the case with the micro-porous polytetrafluorethylene of the type mentioned hereinabove, for example, in which case said layer may be formed in a particularly simple way from a core of determined circumference, by the sequence of steps consisting in:

(a) making two uniform identical flat strips from the micro-porous, bio-compatible flexible synthetic material, each having a longitudinal plane of symmetry and two longitudinal edges the length of which is approximately equal to one-half of said determined circumference, mutually spaced by a width approximately equal to one-quarter of said determined circumference, and joined to each other by two convex semi-circular transverse edges having a diameter approximately equal to one-quarter of said determined circumference.

(b) placing said strips one on each side of the spherical core in a position in which their planes of symmetry are equatorial and mutually perpendicular, (c) folding said strips around the spherical core into a conformation in which they are mutually joined edge-to-edge and complement each other so as to envelop all of the spherical core, and (d) rendering said conformation of said strips around the spherical core permanent.

Step (d) may be achieved by adhesively bonding said strips to the spherical core or by suturing said strips together edge-to-edge, in which case they are preferably sutured to the spherical core also.

The present invention is not limited to a method of manufacturing an intra-orbital implant, but, given that this implant itself has an original and advantageous structure, the invention extends also to implants having this structure, in which the spherical core is integrally covered with said substantially uniform layer of micro-porous, bio-compatible synthetic material intimately mated to the spherical core and formed, for example, from two identical strips of said micro-porous, bio-compatible synthetic material which have respective planes of symmetry that are equatorial and mutually perpendicular and which are joined to each other edge-to-edge, and this irrespective of the way in which such implants are manufactured.

BRIEF DESCRIPTION OF THE DRAWINGS

The invention will be better understood by reference to the following description relating to one embodiment thereof and to the appended drawings which form an integral part of this description.

FIG. 1 is a perspective view of an implant in accordance with the present invention.

FIG. 2 is a view of an implant of this kind in cross-section on an equatorial plane.

DESCRIPTION OF PREFERRED EMBODIMENT

Figure 3:
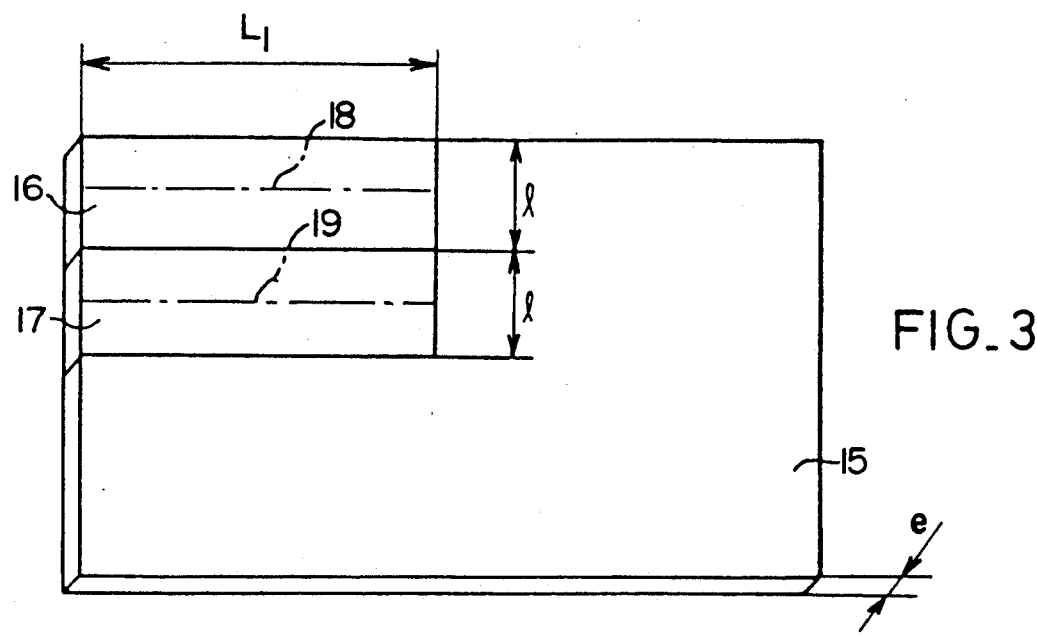
FIG. 3 is a plan view of a sheet of a micro-porous, biocompatible synthetic material that can be used for making the layer coating the core.

Reference will first be made to FIGS. 1 and 2, which show an implant 1 in accordance with the present invention.

This implant 1 has a substantially spherical outside surface 2 of diameter D1 determined empirically by a surgeon according to the dimensions of the enucleated or eviscerated eye.

This surface 2 is defined by the outside surface of a layer 3 of substantially constant thickness e which also has a spherical inside surface 4 of diameter D2 equal to D1 less twice e, in intimate contact with an external surface 5, also spherical and of diameter D2, of a solid core 36 which is thus integrally covered by the layer 3.

The core 36 is made from a bio-compatible synthetic material, preferably a flexible material, such as silicone elastomer; good results have been obtained in trials with a silicone elastomer marketed under the reference Q74535 by the company DOW-CORNING, catalyzed with 2.4 Dichlorobenzoyl, selected because it is well tolerated by the organism, although the scope of the present invention is not exceeded by choosing other bio-compatible synthetic materials for making the core 36.

The layer 3, which is preferably fixed to the core 36 by adhesive bonding and/or suturing, for example, is made from a microporous, bio-compatible synthetic material, for example of the type distributed under the registered trademark GORE-TEX with the reference "GORE-TEX E-PTFE SOFT TISSUE PATCH", and a manufacturing method for which is described in U.S. Pat. No. 3,953,566, with a thickness e in the order of 1 or 2 mm, or of the type distributed by the company IMPRA, with a thickness e of 0.75 mm.

Although it is within the scope of the present invention to make the layer 3 in a single piece, in the example illustrated this layer 3 is made up of two identical strips 6, 7 of said microporous bio-compatible synthetic material which have respective planes of symmetry 18, 19 which are equatorial with reference to the spherical surface 5 of the core 36. This means that they pass through the geometrical center C of this spherical surface 5, and are also mutually perpendicular. The two strips 6 and 7 have respective peripheral edges 8, 9 conferring on these two strips 6, 7 identical contours, such that they adjoin each other by their edges 8, 9, to be more precise along all of these edges 8 and 9, in order to cover completely the surface 5 of the core 6 without any additional thickness in layer 3.

The two strips 6 and 7 are fastened to each other, and preferably to the core 36, by any appropriate means. For example, if the respective surfaces of the strips 6 and 7 in contact with the surface 5 of the core 36, i.e., jointly defining the surface 4 of the layer 3, are designated 10 and 11, these surfaces 10 and 11 of the strips 6 and 7 may be adhesively bonded over all of their surface to the surface 5 of the core 36 by an appropriately chosen adhesive; good results have been achieved in trials using the DOW-CORNING adhesive reference Q72947 in the case of a core 36 made from the silicone elastomer of the type indicated hereinabove and strips 6, 7 of the layer 3 made from micro-porous polytetrafluoroethylene of either type indicated hereinabove. The two strips 6 and 7 may also be assembled edge-to-edge by overcast suturing 12 using a non-absorbable thread 13, of polyester, for example; this overcast suturing 12 preferably comprises from place to place along the edges 8 and 9 equally spaced points 14 of deeper penetration encompassing not only the material of the strips 6 and 7 but also the material of the core 36, in an area localized near the surface 5 of the latter.

The strips 6 and 7 may be manufactured in such a way as to feature an inherently spherical conformation of their surfaces 10 and 11, such that these surfaces 10 and 11 mate exactly with the surface 5 of the spherical core 36.

However, if the micro-porous, bio-compatible synthetic material chosen is flexible, it is also possible to manufacture the strips 6 and 7 in a simple and economical way, but nevertheless with an acceptable degree of approximation, by cutting them out from a flat film of this material having the thickness e required for the layer 3, as will now be described with reference to FIGS. 3 to 8.

To this end, as shown in FIG. 3, one begins by cutting out from the film 15 two identical flat strips 16, 17 having the thickness e and a rectangular shape as seen in plan view, of length $L_1$ and of width 1 with (where $\pi.D_2$ corresponds to the circumference of the core 36):

$1 = \frac{1}{4}.\pi.D_2$, $L_1 = 3.1$.

Each of the strips 16 and 17 has along its longest plane dimension $L_1$, perpendicularly to its smallest plane dimension 1, a longitudinal plane of symmetry which will define respectively the plane of symmetry 18 of the strip 6 or the plane of symmetry 19 of the strip 7, and therefore has the reference number 18 where the strip 16 is concerned or the reference number 19 where the strip 17 is concerned.

Figure 4:
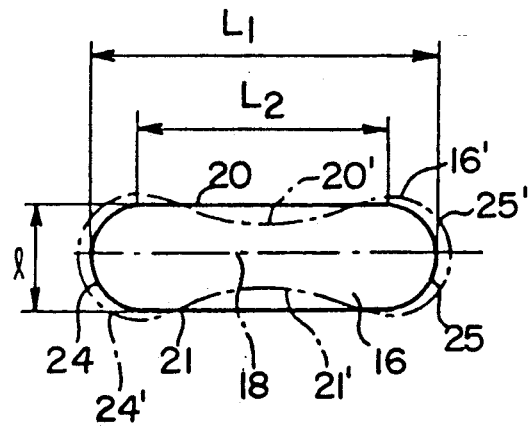
FIGS. 4 and 5 are plan views of two strips taken from this sheet in order to manufacture said layer.
Figure 5:
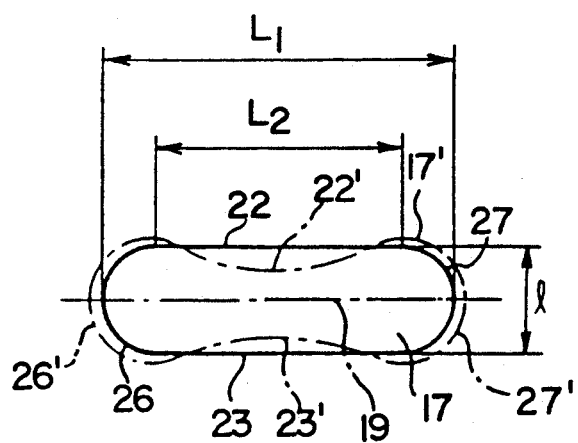

Then, as shown in FIGS. 4 and 5, the two strips 16 and 17 are rounded in precisely the same way so as to have two mutually parallel rectilinear longitudinal edges of length $L_2$ equal to $2 \times 1$, mutually spaced by the width 1 (namely the edges 20 and 21 of the strip 16 and the edges 22 and 23 of the strip 17), and two convex semicircular transverse edges of diameter 1, centered on the corresponding respective plane of symmetry 18, 19 and joining together the afore-mentioned rectilinear edges (namely, the edges 24 and 25 where the strip 16 is concerned and the edges 26 and 27 where the strip 17 is concerned).

Figure 6:
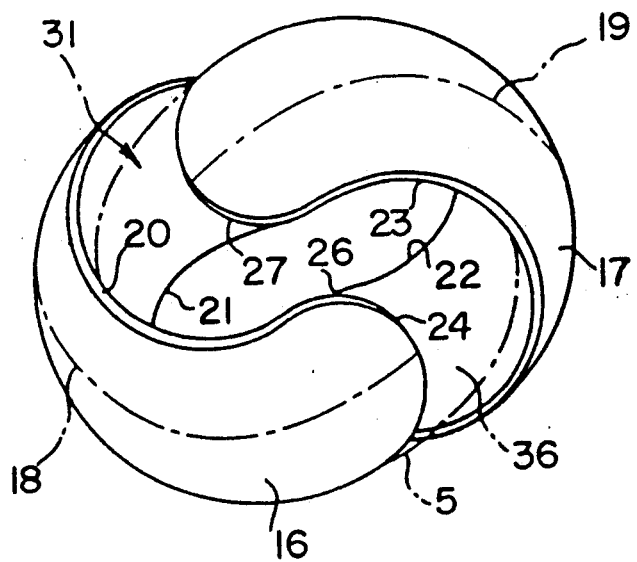
FIG. 6 shows the fitting of these strips around the core in a perspective view.

As shown in FIG. 6, where the core 6 and its surface 5 are shown in chain-dotted outline, in order to produce the implant 1 the strips 16 and 17 are placed each on a respective side of the core 6 with their planes of symmetry 18 and 19 positioned perpendicularly to each other and passing through the center of the core 36 (not shown in this figure).

Figure 7:
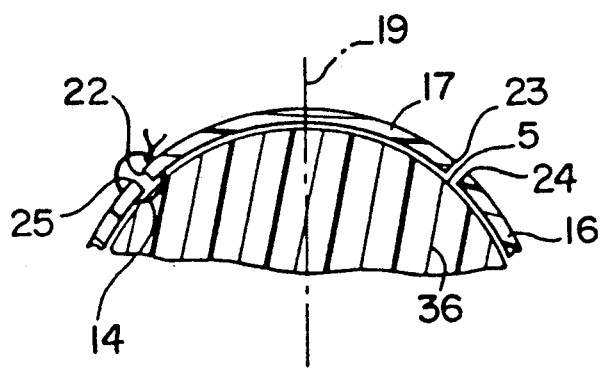
FIG. 7 is a partial view in cross-section analogous to that of FIG. 2, and illustrates an initial phase of fastening the two strips to the core.
Figure 8:
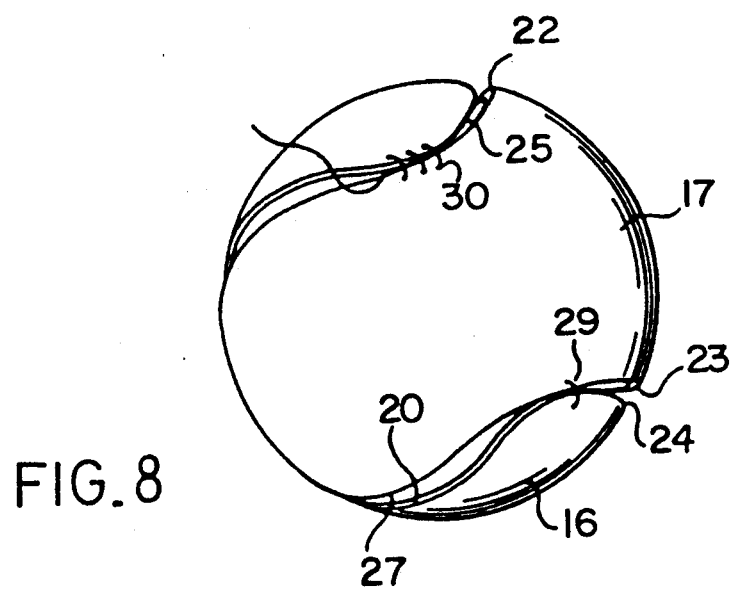
FIG. 8 is a perspective view analogous to that of FIG. 1 illustrating this initial fastening phase.

Then, retaining this position of the planes 18 and 19, the strips 16 and 17 are deformed from their initial flat conformation by curving them in their planes of symmetry 18 and 19 and transversely to these planes until the edges 26 and 27 of the strip 17 are brought into contact with the respective edges 21 and 20 of the strip 16 and the edges 24 and 25 of this strip 16 are brought into contact with the respective edges 23 and 22 of the strip 17, as shown in FIGS. 6 to 8.

The edges intended to come into contact with each other in this way are first juxtaposed in areas immediately adjacent the planes 18 and 19 and, if the strips 16 and 17 are intended to be sutured together to constitute the strips 6 and 7 of the layer 3, the strips 16 and 17 are held together in these initial juxtaposition areas by a few tacking sutures 29, 30 using a nonabsorbable thread, for example of 5/0 gauge polyester, as shown in FIG. 8. Overcast suturing with the same thread then makes it possible to complete the edge-to-edge joining of the two strips 16 and 17, which are progressively molded to the surface 5 of the core 36 in such a way as to mate to it optimally and to constitute the two strips 6 and 7 of the layer 3, complementing each other so as to cover all of the surface 5 of the core 36.

As already stated hereinabove and as shown in FIG. 7, which shows the overcast suturing in progress, this overcast suturing encompasses not only the strips 16 and 17 but also the core 36 by virtue of the deeper penetration points 14 which, by fastening the strips 16 and 17 (or 6 and 7) to the core 36, make it possible for the latter to contribute to the overall mechanical strength of the implant 1.

In addition to or instead of suturing together the strips 16 and 17 to constitute the strips 6 and 7 of the layer 3 covering the core 36, the strips 16 and 17 may be fixed by adhesive bonding to localized areas or preferably the whole of the surface 5 of the core 36. To this end, as schematically represented by an arrow 31 in FIG. 6, the surface 5 of the core 36 is locally or preferably integrally covered with an appropriate adhesive, of the type indicated hereinabove, for example, before folding down onto this surface 5 the strips 16 and 17 disposed so that their median planes 18 and 19 are equatorial, relative to the core 36, and mutually perpendicular. Alternatively, the strips 16 and 17 could themselves be coated with adhesive; the strips 16 and 17 are then folded down as stated hereinabove onto the surface 5 of the core 36 so as to juxtapose them edge-to-edge.

There is obtained in this way the implant 1 shown in FIG. 1 and 2 of which the strips 6 and 7 of the layer 3 are constituted by the strips 16 and 17, respectively. It will be noted that the shape of the strips 16 and 17 described with reference to FIG. 3 to 5 implies the possibility of plastic deformation thereof to enable them to be juxtaposed edge-to-edge by molding them around the spherical core 36. The micro-porous polytetrafluoroethylene mentioned hereinabove does offer this possibility; experience has shown that the plastic deformation to which the strips 16 and 17 are subjected as they are fitted around the spherical core 36 is sufficiently small to cause only negligible variations in the thickness of the strips 16 and 17, in other words to result in only negligible asphericity of the surface 2 of the layer 3 of the implant 1 obtained.

However, if the material constituting the strips 16 and 17 does not have sufficient ability for plastic deformation or, although it has sufficient aptitude of this kind, the surface 2 of the layer 3 is required to be perfectly spherical, then the strips 16 and 17 may be cut out with the shape described with reference to FIGS. 3 and 4 and shown in full outline in those figures, but with a shape known from other arts and shown in chain-dotted outline at 16' in FIG. 4 and at 17' in FIG. 5, respectively. This shape is symmetrical relative to the plane 18 where the strip 16' is concerned and relative to the plane 19 where the strip 17' is concerned, is characterized by two convex identical transverse edges, respectively 24', 25' and 26', 27', of approximately circular arc shape respectively centered on the plane 18 and on the plane 19 and with a diameter slightly greater than 1 and subtending an angle slightly greater than 180°, these two transverse edges merging with each other through two concave curvilinear identical longitudinal edges, respectively 20', 21 and 22', 23, having a length approximately equal to $L_2$ and defining between them a narrower section with a minimum transverse dimension slightly less than 1. Each strip 16', 17' has a longitudinal dimension slightly greater than $L_1$ and corresponding to the difference between the circumference of the surface 5 of the spherical core 6 and said minimum transverse dimension. The placing of the strips 16' and 17' around the spherical core 36 and their fixing thereto are then effected in the way described in connection with the strips 16 and 17 to obtain an implant 1 of the type shown in FIGS. 1 and 2, the strips 16' and 17' of which constitute the strips 6 and 7, respectively.

The implant 1 obtained in this way is then sterilized, using ethylene oxide, for example, and then, following a degassing period of approximately three weeks, may be implanted after enucleation or evisceration.

In the case of an application to enucleation, as much as possible of the conjunctiva is retained during nucleation to retain sufficient depth of the upper and lower fornices. After dissection of the tenon, each rectus muscle intended to be reinserted into the implant is isolated from the sclera and leaded with a non-absorbable thread, of 5/0 gauge polyester for example. The oblique muscles are then sectioned, and can obviously be reinserted into the implant also, and in this case they are also charged with a non-absorbable thread. The optical nerve is then sectioned and the eye enucleated; it is essential to achieve perfect haemostasis and total disinfection of the working area. Then, using a sterile dummy implant for calibration, for example, the quantity and quality of the tenon and the conjunctiva are evaluated to determine the diameter $D_1$ of the implant 1 to be used according to the dimensions of the orbital cavity; the diameter $D_1$ generally varies between approximately 14 and 20 mm. The implant 1 is then fitted, suturing the previously charged muscles, namely, at least the four rectus muscles and preferably also the oblique muscles, directly to it, i.e., to the layer 3 and preferably also, through the latter, to the core 36 by means of the deeper penetration points of the kind shown at 14 in FIG. 7. Vascular and fibroblastic invasion of the material of the layer 3 will later take place, reinsertion insertion of the muscle fibers gradually taking place and reinforcing the anchoring of the muscles onto the implant. Finally, the tenon and the conjunctiva are closed at separate points using 5/0 gauge absorbable thread, taking care not to tension the stitches. A loose cold compress serum type dressing held in place by a circumferential bandage is preferable for the 24 hours following the operation. Local or generalized antibiotic and/or anti-inflammatory treatment for ten days leads to rapid reduction of post-operative oedema.

In the case of an application to evisceration, the sclera is kept together with the muscles attached to it and the implant 1 is inserted into the sclera which is incised laterally, the size of the implant being generally larger than that of the balls usually employed in an application of this kind. A dome of the layer 3 is left uncovered by the sclera, in a circular area corresponding to an anterior area of the enucleated eye, so that the sclera retains its natural form, and the sclera is stitched onto the implant, by means of the layer 3 of the latter and preferably also by means of the core 36 through the layer 3, by self-concealing overcast suturing or separate sutures using a non-absorbable thread, of 5/0 gauge polyester, for example, around the dome of the layer 3 not covered by the sclera. This region may also be sutured using an absorbable thread, with, for example, two suturing points using non-absorbable thread between the implant 1 and the sclera in the deeper areas of the latter, in the region of the ends of the lateral incisions. The tenon and the conjunctiva are then closed over the dome of the layer 3 exposed in this way, as described hereinabove with reference to enucleation, and with the same precautions being taken as to the suturing. The dome of the layer 3 which is not covered with the sclera will then be colonized by the overlaying tissue, namely, the tenon and the conjunctiva, and where overcast suturing using an absorbable thread is employed around this dome, such colonization may take over from the absorbable thread to retain the sclera onto the implant.

In either application, approximately three to four weeks after the implant is fitted, the patient may be sent to a prosthesis oculist who makes and fits to the conjunctiva a prosthesis reproducing the external appearance of the enucleated eye, in the usual way by carefully molding the prosthesis, it is enabled to move in unison with the implant.

What is claimed is:

1. Method of manufacturing an intra-orbital implant intended to be accommodated in an orbital cavity after enucleation or evisceration and to be joined to oculo-motor muscles, using a spherical core of predetermined circumference in a bio-compatible flexible, suturable, synthetic material, said method comprising the steps of
   (a) making two uniform identical flat strips from a micro-porous bio-compatible suturable flexible synthetic material capable of plastic deformation, each of said strips having a longitudinal plane of symmetry and two longitudinal edges the length of which is approximately equal to one-half of said predetermined circumference, mutually spaced by a width approximately equal to one-quarter of said predetermined circumference and joined to each other by two convex semi-circular transverse edges having a diameter approximately equal to one-quarter of said predetermined circumference;
   (b) placing said strips one on each side of the spherical core in a position in which their longitudinal planes of symmetry contain a spherical center of said core and are mutually perpendicular;
   (c) folding said strips around the spherical core into a conformation in which they are mutually joined edge-to-edge and complement each other so as to envelop all of the spherical core; and
   (d) rendering said conformation of said strips around said spherical core permanent.

2. Method according to claim 1, wherein step (d) is effected by attaching said strips to said spherical core.

3. Method according to claim 2, wherein step (d) is effected by adhesively bonding said strips to said spherical core.

4. Method according to claim 1, wherein step (d) is effected by suturing said strips together edge-to-edge.

5. Method according to claim 2, wherein step (d) is effected by suturing said strips together edge-to edge and to the spherical core.

6. Method according to claim 1, wherein said bio-compatible synthetic material of the spherical core is a silicone elastomer.

7. Method according to claim 1, wherein said micro-porous bio-compatible synthetic material is a micro-porous polytetrafluorethylene.

8. Intra-orbital implant adapted to be accommodated in an orbital cavity after enucleation or evisceration and to be joined to oculo-motor muscles, and comprising to this end a bio-compatible, flexible, suturable synthetic material spherical core integrally coated with a substantially uniform layer of a micro-porous bio-compatible synthetic material intimately mated to said spherical core, said layer being formed from two identical strips of said micro-porous bio-compatible synthetic material which have median planes each containing a spherical center of said core and are joined to each other edge-to-edge.

9. Intra-orbital implant according to claim 8, wherein said strips are fastened to said core.

10. Implant according to claim 9, wherein said strips are adhesively bonded to said core.

11. Implant according to claim 8, wherein said strips are sutured together edge-to-edge.

12. Implant according to claim 9, wherein said strips are sutured together edge-to-edge and to the core.

13. Implant according to claim 8, wherein said bio-compatible synthetic material of said spherical core is a silicone elastomer.

14. Implant according to claim 8, wherein said micro-porous bio-compatible synthetic material is a micro-porous polytetrafluorethylene.

15. Implant according to claim 8, wherein the material constituting said layer is capable of plastic deformation.

* * * * *